United States Patent [19]

Osenkarski

[11] 4,213,463
[45] Jul. 22, 1980

[54] BODY ELECTRODE WITH INDICATOR TO ENSURE OPTIMAL SECUREMENT

[75] Inventor: Paul D. Osenkarski, Orchard Park, N.Y.

[73] Assignee: Graphic Controls Corporation, Buffalo, N.Y.

[21] Appl. No.: 927,127

[22] Filed: Jul. 24, 1978

[51] Int. Cl.² ............................................. A61B 5/04
[52] U.S. Cl. ............................... 128/639; 128/303.13; 128/798; 73/762; 116/322
[58] Field of Search .......... 128/2.06 E, 2.1 E, 303.13, 128/404, 410, 411, 416, 417, 418, 169, 384, 327, 639-641, 644, 798, 802, 803; 73/760, 762; 33/125 R; 116/322, 321, 278, 335; 40/491

[56] References Cited

U.S. PATENT DOCUMENTS

| | | | |
|---|---|---|---|
| 1,759,219 | 5/1930 | Bowlus | 73/760 |
| 1,982,304 | 11/1934 | Holden | 33/125 R |
| 3,431,885 | 3/1969 | Miklas | 40/491 |
| 3,572,091 | 3/1971 | McFarland | 73/762 X |
| 3,613,679 | 10/1971 | Bijou | 128/169 |
| 3,972,329 | 8/1976 | Kaufman | 128/2.06 E |
| 4,090,313 | 5/1978 | Morse | 40/491 |
| 4,092,985 | 6/1978 | Kaufman | 128/417 X |

Primary Examiner—Lee S. Cohen
Attorney, Agent, or Firm—Michael G. Berkman

[57] ABSTRACT

A body electrode including a visual indicator to ensure optimal parallel positioning and electrical current distribution between the electrode and the body. The indicator comprises a flap imprinted with alternating areas of green and red indicia, and an exterior sheet overlying the flap and defining three windows. The flap and the exterior sheet are attached at longitudinally spaced locations to a stretchable, insulating cover sheet. Stretching the electrode to a predetermined optimal degree of tension aligns green indicia with the windows, and presence of red indicia in the windows indicates either excessive or insufficient applied tension.

11 Claims, 7 Drawing Figures

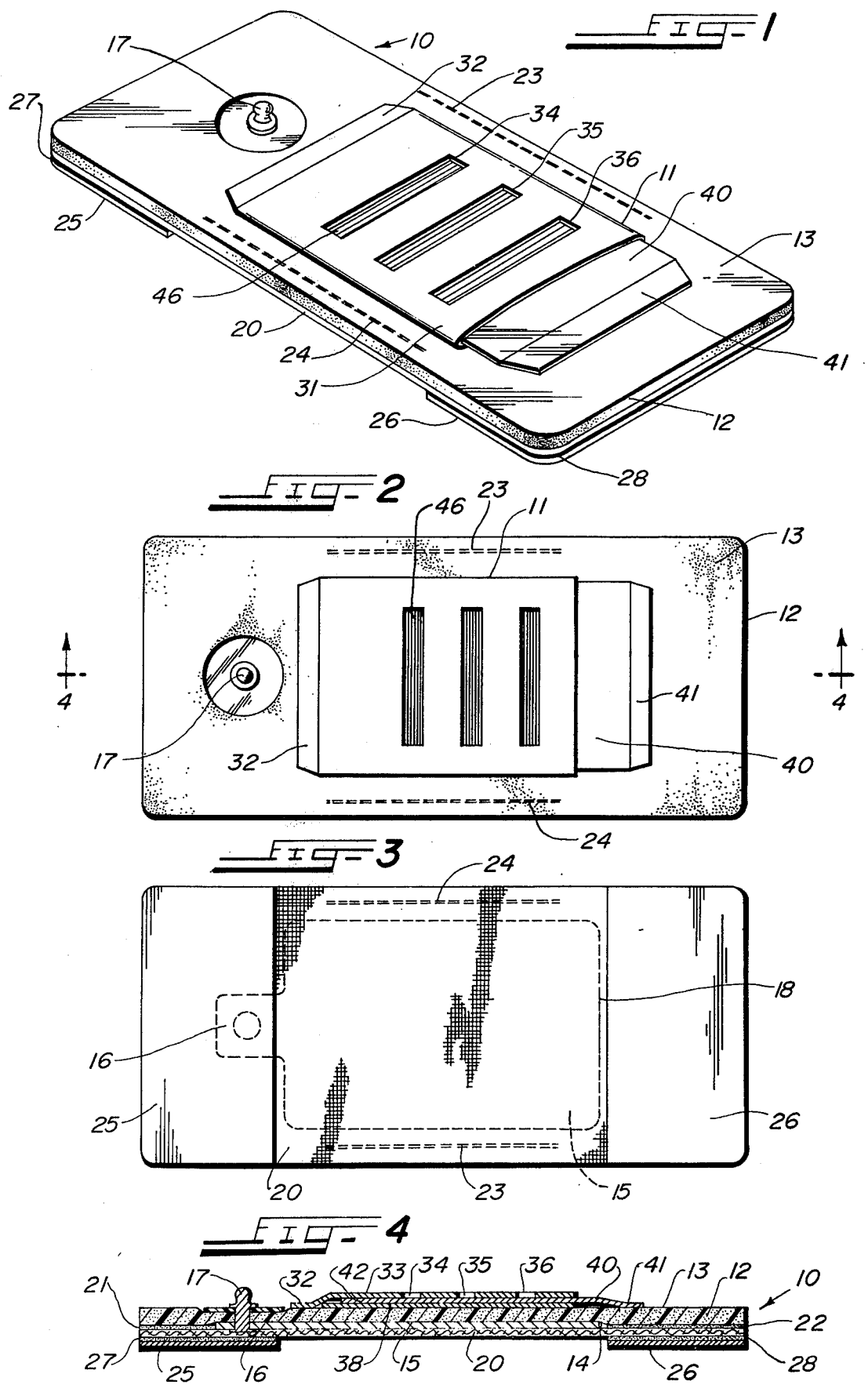

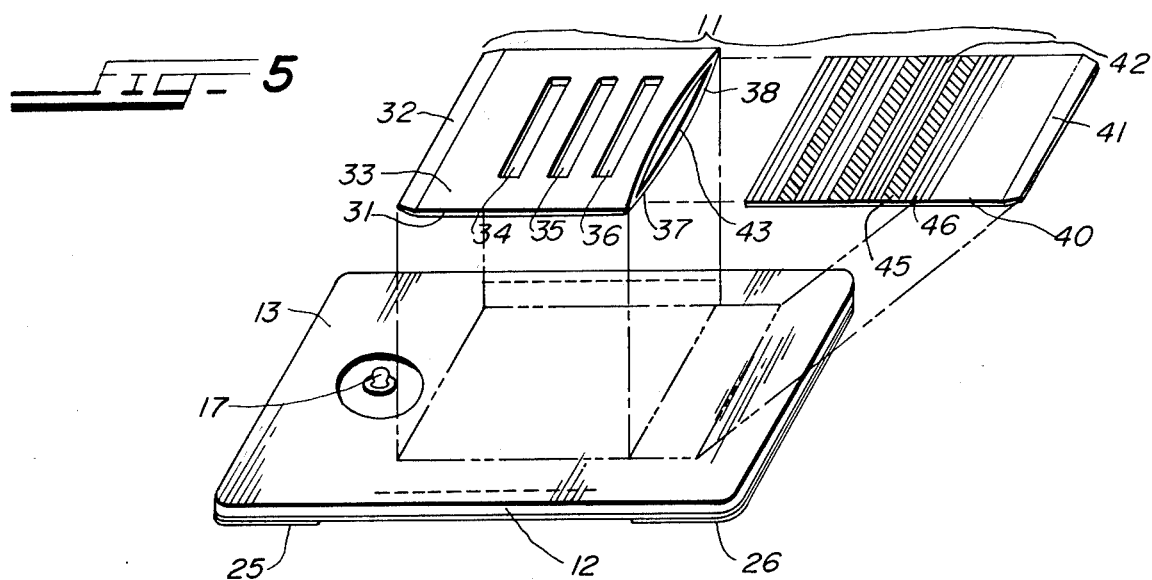
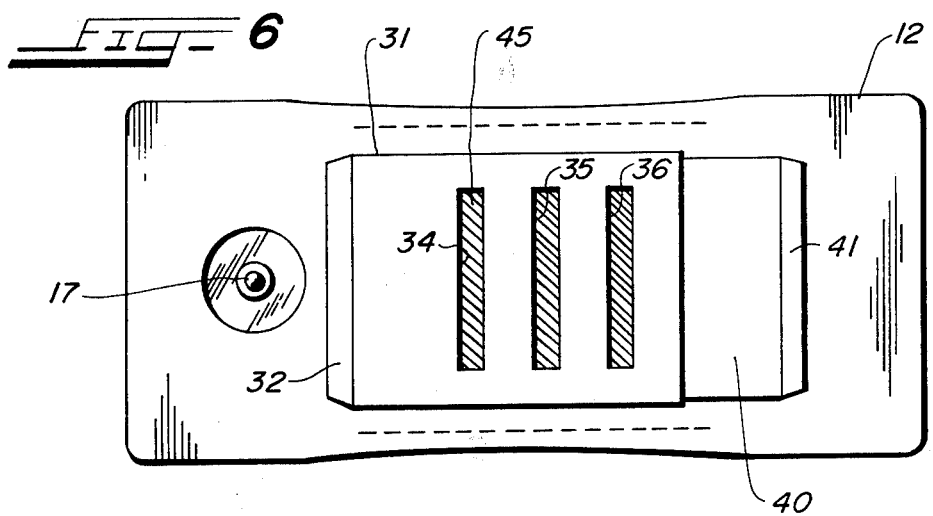
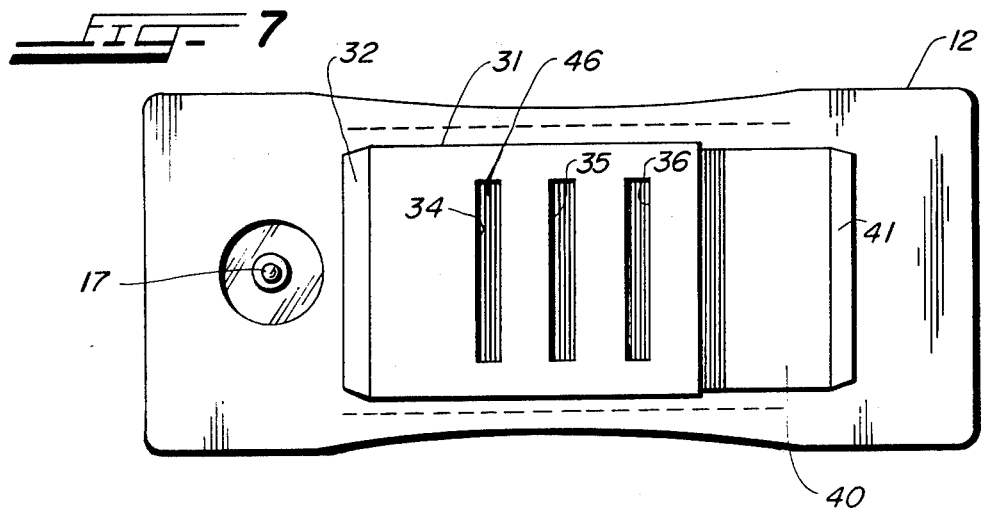

BODY ELECTRODE WITH INDICATOR TO ENSURE OPTIMAL SECUREMENT

BACKGROUND OF THE INVENTION

The present invention relates to body electrodes of the type applied to the trunk and limbs of patients in connection with surgical, therapeutic and diagnostic procedures using electromedical instruments. Dispersive electrodes are used to complete electrical circuits at the point of body contact with such instruments in order to distribute current density over a larger area. Dispersion of electrical current over increased area minimizes tissue heating problems which may result in skin necrosis.

Dispersive body electrodes typically include an electrically conductive inner portion having a surface area of several square inches, an electrically insulating cover sheet overlying the inner portion, and an adhesive securing the cover sheet to the skin. An electrically conductive gel is usually applied to the skin to optimize electrical contact with the conductive inner portion. The cover sheet is a stretchable, resilient sheet of a foam plastic material which must be stretched to force the conductive inner portion into parallel relationship with the skin surface and to force out residual air pockets.

Problems may arise with such body electrodes if medical personnel stretch the cover sheet either too little or too far. When an electrode sheet is stretched to its optimal degree, the conductive inner portion is generally parallel to the skin surface so that electrical capacitance and current distribution are substantially uniform. When the cover sheet is stretched too little, the conductive inner portion and skin surface are likely to become nonparallel, thereby producing hot spots in areas of increased capacitance and residual air pockets or gaps in other areas. When the cover sheet is stretched too far, excessive tension on the cover sheet tends to peel it away from adhesion with the body surface.

SUMMARY OF THE INVENTION

It is a principal object of the present invention to provide a dispersive body electrode with indicator means for visually demonstrating either excessive or insufficient stretch tension applied longitudinally to a stretchable resilient cover sheet of the electrode. Optimal electrical current distribution between the skin and an electrically conductive inner portion of the electrode is thereby ensured.

Additional objects and advantages of the present invention will become apparent to persons skilled in the art from the following specification, taken in conjunction with the drawings.

The foregoing objective of the invention is accomplished by providing a dispersive body electrode with an attached indicator showing green colored indicia when optimum tension is applied longitudinally to a cover sheet, and either red colored indicia or a mixture of red and green indicia when the tension applied is either excessive or insufficient.

BRIEF DESCRIPTION OF THE DRAWINGS

FIG. 1 is a perspective view of a body electrode of the invention;

FIG. 2 is a top plan view of the body electrode of FIG. 1;

FIG. 3 is a bottom plan view of the body electrode of FIG. 1;

FIG. 4 is a lateral cross-sectional view taken along the lines 4—4 of FIG. 2;

FIG. 5 is an exploded perspective view of the body electrode of the invention;

FIG. 6 is a top plan view of the body electrode of FIG. 5, showing alignment between three windows of the indicator and green indicia on the indicator flap; and FIG. 7 is a top plan view of the body electrode of FIG. 5, showing red indicia in all three windows of the indicator.

DESCRIPTION OF A PREFERRED EMBODIMENT

A dispersive body electrode 10 of the invention is illustrated in FIGS. 1–5. The electrode 10 is provided with an indicator means or visual indicator 11 for ensuring optimal electrical current distribution with respect to the body of a patient to whom the electrode 10 is applied.

The electrode 10 includes a manually stretchable, electrically insulating cover sheet 12. In the preferred embodiment shown this cover sheet 12 is formed from a foam plastic material. The cover sheet 12 has an outer surface 13 facing away from the body of a patient (not shown) and an inner surface 14 facing toward the body.

The electrode 10 forms part of an electrical circuit which includes an electromedical instrument comprising a voltage source; an active probe on a lead wire from the instrument to the body of patient; the patient's body; a dispersive electrode; and a dispersive electrode cable connected to the instrument. Only the electrode 10 is illustrated in the drawings. The electrode 10 is maintained in electrically conductive relation to the patient's body by an inner conductive plate or inner portion 15 which is an aluminum foil having a thickness of about 10 mils in the preferred embodiment shown. Other conductive metals such as copper, stainless steel, and iron may be used instead of aluminum.

The conductive plate 15 includes a longitudinally outwardly extending ear 16 narrower than a principal portion of the plate 15. A metal terminal or terminal means 17 is connected to the ear 16. The terminal 17 projects outwardly of the cover sheet 12 for interconnection with a cable (not shown) leading to the instrument. Optionally, the conductive plate 15 may be connected directly to the cable. The ear 16 is secured to the cover sheet 12 but a longitudinally opposed end portion 18 of the plate 15 is not connected to the cover sheet 12 or other portions of the electrode 10.

A porous interior sheet 20 is secured to opposed longitudinal end portions of the cover sheet 12 by areas of adhesive 21, 22. Laterally opposed side portions of the interior sheet 20 are also fused to the cover sheet 12 along two parallel lines of adhesive 23, 24. The interior sheet 20 is a thin sheet of crepe polyester cloth porous to electrically conductive gels. Other suitable materials are porous paper and porous open-celled foam plastics.

The electrode 10 is fastened to the body of a patient by peeling away cover slips 25, 26 from areas of pressure-sensitive adhesive 27, 28. These areas 27, 28 are then impressed upon the skin, conforming the electrode 10 to contour of the patient's body while stretching the electrode 10 longitudinally.

Referring now more particularly to FIGS. 5–7, the electrode 10 further comprises an indicator means or indicator 11 attached to an outer surface 13 of the cover sheet 12. The indicator 11 includes an envelope 31 having a marginal edge portion 32 attached to the cover sheet 12, and an exterior sheet 33. The exterior sheet 33 defines three laterally elongated through windows or viewing zones 34, 35, 36. Optionally, windows may be cut from the exterior sheet as circles, stars, or other geometric patterns. These other patterns would be used if the indicator 11 is applied to an electrode that is stretchable laterally as well as longitudinally. Lateral flange portions 37, 38 of the exterior sheet 33 are folded laterally inwardly and are joined together adjacent the cover sheet 12.

The indicator 11 further includes a flap 40 having a fixed or first portion 41 attached to the cover sheet 12 and a free or principal portion 42 inserted through an end opening 43 in the envelope 31. An upper surface of the flap 40 is imprinted with alternating laterally elongated areas of green indicia 45 and red indicia 46.

When no longitudinal tension is applied to the cover sheet 12, red indicia 46 are observed through the windows 34, 35, 36 as shown in FIGS. 1–2. When the cover sheet 12 is stretched to a length corresponding to a predetermined optimal degree of tension all green indicia 45 are seen, as shown in FIG. 6. In this position the conductive plate 15 is maintained generally parallel to the skin surface so that electrical capacitance and current distribution are substantially uniform over the entire area of the plate 15. When the cover sheet 12 is stretched to a lesser degree of tension the plate 15 becomes non-parallel to the skin surface, thereby resulting in hot spots in areas of increased capacitance where the plate 15 and skin surface are too close, and residual air pockets or gaps in other areas. When the cover sheet 12 is stretched excessively, as shown in FIG. 7, all red indicia 46 will appear in the windows 34, 35, 36. In this position increased tension on the cover sheet 12 tends to peel it away from adhesion with the skin surface. Although not illustrated, a mixture of red indicia 46 and green indicia 45 is observed when the cover sheet 12 is stretched to other, nonoptimal degrees of tension.

The indicator means 11 of the present invention may also be manufactured separately from the electrode 10. In the separately manufactured indicator means 11, a first area of pressure-sensitive adhesive or adhesive means is applied to an underside of the marginal edge 32 of the envelope 31. A second area of pressure-sensitive adhesive or adhesive means is applied to an underside of the fixed portion 41 of the flap 40. The indicator means 11 is adhered to the electrode 10 by impressing both adhesive areas against an outer surface 13 of the cover sheet 12. This form of my invention may also have utility in non-electrical medical instruments and devices such as blood pressure cuffs.

The indicator means 11 of my invention can be used as a component of an electrical switch for turning off the current source in an electromedical instrument when an improper degree of tension is applied to the cover sheet 12. For example, if the electrode 10 fell off the body of a patient or if the degree of tension on the cover sheet 12 became less than a predetermined value, the indicator means 11 would trigger a switch turning off the current source.

While the foregoing description of my invention has been made with reference to a preferred embodiment, numerous changes and alterations can be made therein without departing from the spirit and scope of the invention as set forth in the following claims.

What is claimed is:

1. A body electrode for use with an electromedical instrument and removably attachable to a person's body, said electrode comprising
    a manually stretchable, electrically insulating cover sheet having an outer surface adapted to face away from the body, and an inner surface adapted to face toward the body;
    electric circuit means for maintaining the body in electrically conducting relation to an electromedical instrument, said electric circuit means comprising an electrically conductive inner portion adjacent said inner surface, and terminal means connected in an electrically conducting relation to said inner portion; and
    indicator means to ensure proper manual adjustment of tension on said cover sheet to optimize electrical current distribution between said inner portion and the body, said indicator means comprising
    an exterior sheet attached to said outer surface of said cover sheet and defining a viewing zone; and
    a flap having a fixed portion attached to said outer surface of the cover sheet and a principal portion longitudinally shiftable and freely slidable between said exterior sheet and said cover sheet upon longitudinal stretching of said cover sheet, said flap including an outer surface imprinted with indicia contrasting visibly with surrounding portions of said outer surface of said flap, said indicia being visibly aligned with said viewing zone upon longitudinally stretching said cover sheet to apply a predetermined optimal degree of tension, and wherein misalignment between said viewing zone and said indicia reveals excessive and insufficient stretch tension applied to said cover sheet.

2. The body electrode of claim 1, wherein said fixed portion constitutes a marginal edge portion of the flap spaced longitudinally of said exterior sheet.

3. The body electrode of claim 2, wherein said exterior sheet is attached to said cover sheet along a marginal edge portion spaced longitudinally of said fixed portion of the flap.

4. The body electrode of claim 1, wherein said exterior sheet is wider than said flap, and said exterior sheet further comprises a pair of lateral flange portions folded laterally inwardly between the cover sheet and the flap to define an envelope retaining the flap in longitudinal alignment with said exterior sheet.

5. The body electrode of claim 1, wherein said viewing zone comprises a window means formed in said exterior sheet.

6. The body electrode of claim 5, wherein said window means comprises a plurality of laterally elongated windows, and said indicia comprise a plurality of laterally elongated indicia.

7. The body electrode of claim 1, wherein indicia on said flap corresponding to alignment with said viewing zone are green, and surrounding portions of said flap corresponding to misalignment with said viewing zone are a color contrasting visibly with green.

8. The body electrode of claim 7, wherein said color contrasting visibly with green is red.

9. The body electrode of claim 1, wherein said cover sheet is formed from a longitudinally resilient, foam plastic.

10. An indicator and a stretchable cover sheet therefor for ensuring a predetermined, optimal degree of stretch tension on said cover sheet in an electrode removably attachable to the body of a person, the combination comprising
- a cover sheet,
- an exterior sheet of said indicator, said exterior sheet defining a viewing zone; means attaching said exterior sheet to said cover sheet at an outer surface thereof, said cover sheet being longitudinally stretchable to optimize current distribution between the electrode and the body, and
- a flap of said indicator, means attaching said flap to said cover sheet at said outer surface thereof, said flap having a first portion longitudinally spaced from said exterior sheet, and a principal portion longitudinally shiftable and freely slidable between said exterior sheet and said cover sheet upon stretching said cover sheet longitudinally, said flap including an outer surface imprinted with indicia contrasting visibly with surrounding portions of said outer surface of said flap, said indicia being visibly aligned with said viewing zone upon longitudinally stretching said cover sheet to apply a predetermined optimal degree of tension, and wherein misalignment between said viewing zone and said indicia reveals excessive and insufficient stretch tension applied to said cover sheet.

11. The combination of claim 10, and further comprising
- first adhesive means for adhering said exterior sheet to said cover sheet, and
- second adhesive means for adhering said flap to said cover sheet, said second adhesive means being spaced longitudinally of said first adhesive means.

* * * * *